United States Patent [19]

Grayzel et al.

[11] 4,102,331
[45] Jul. 25, 1978

[54] DEVICE FOR TRANSMITTING ELECTRICAL ENERGY

[75] Inventors: Joseph Grayzel, Englewood; William Terrell, Scotch Plains, both of N.J.

[73] Assignee: Datascope Corporation, Paramus, N.J.

[21] Appl. No.: 725,326

[22] Filed: Sep. 21, 1976

[51] Int. Cl.² ............................................. A61B 5/04
[52] U.S. Cl. .................. 128/2.1 E; 128/417; 128/DIG. 4
[58] Field of Search .............. 128/2.06 E, 2.1 R, 404, 128/410, 411, 416, 417, 418, 419 P, DIG. 4

[56] References Cited

U.S. PATENT DOCUMENTS

| | | | |
|---|---|---|---|
| 3,426,746 | 2/1969 | Seamans, Jr. | 128/2.06 E |
| 3,518,984 | 7/1970 | Mason | 128/2.06 E |
| 3,545,432 | 12/1970 | Berman | 128/2.06 E |
| 3,565,059 | 2/1971 | Hauser et al. | 128/2.06 E |
| 3,610,229 | 10/1971 | Zenkich | 128/2.06 E |
| 3,845,757 | 11/1974 | Weyer | 128/2.1 E |
| 3,865,099 | 2/1975 | Robichaud | 128/2.1 E |
| 3,964,469 | 6/1976 | Manley | 128/2.1 E |
| 3,972,329 | 8/1976 | Kaufman | 128/2.06 E |

FOREIGN PATENT DOCUMENTS

| | | | |
|---|---|---|---|
| 122,258 | 2/1972 | Denmark | 128/2.06 E |
| 1,219,017 | 1/1971 | United Kingdom | 128/419 P |
| 176,033 | 12/1965 | U.S.S.R. | 128/417 |

Primary Examiner—Robert W. Michell
Assistant Examiner—Lee S. Cohen
Attorney, Agent, or Firm—Steinberg & Blake

[57] ABSTRACT

A device which is adapted to transmit electrical energy between an electrical instrument and a living body such as a human body. The device includes a support which has an outer face adapted to be placed in engagement with a surface such as a human skin surface, while the support has an outer periheral edge surrounding the latter outer face thereof and the support being formed inwardly of its outer peripheral edge with an opening extending at least partly into the support from its outer face. An electrically-conductive gel is situated in the latter opening and is at least partly exposed at the outer face of the support so as to be capable of engaging and making electrical contact with the surface which is engaged by the outer face of the support. At least one carbon yarn has a portion situated in this gel for making electrical contact therewith, and an insulation covers the yarn at the region of its portion which is situated in the gel. This insulation is carried by the support so as to support the carbon yarn through the insulation. The yarn together with the insulation have a length sufficiently great to extend through a substantial distance beyond the support, and the yarn carries at an end distant from the portion which is in the gel a contact for connection to an electrical instrument or the like.

16 Claims, 14 Drawing Figures

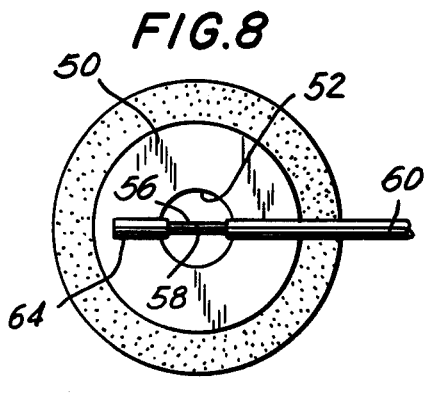
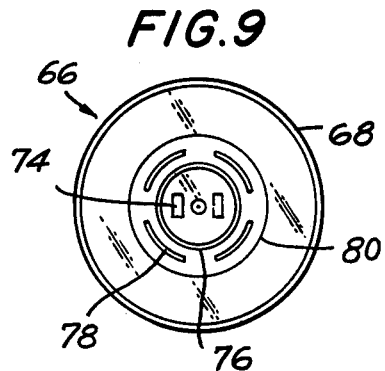
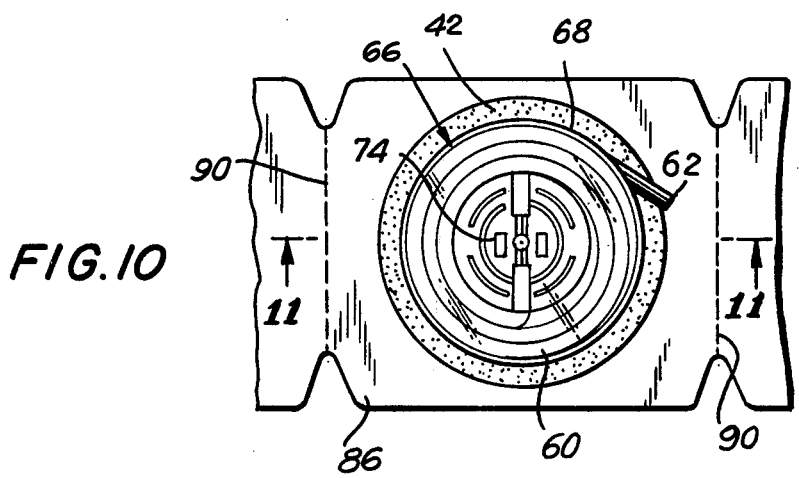
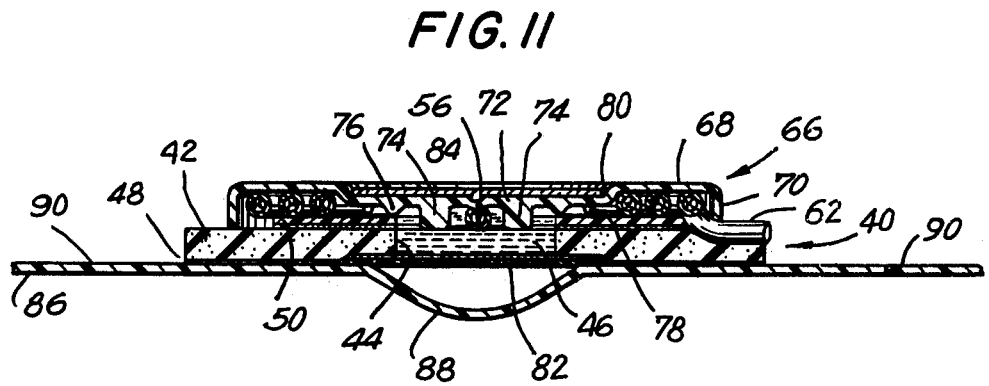

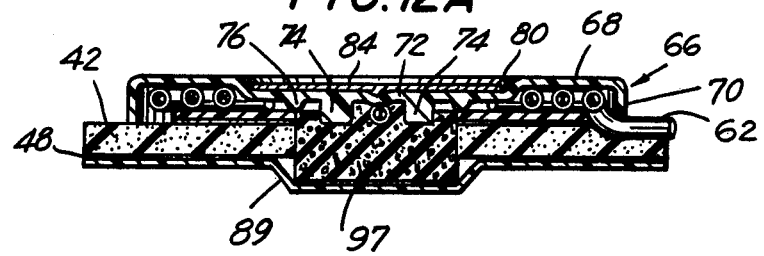
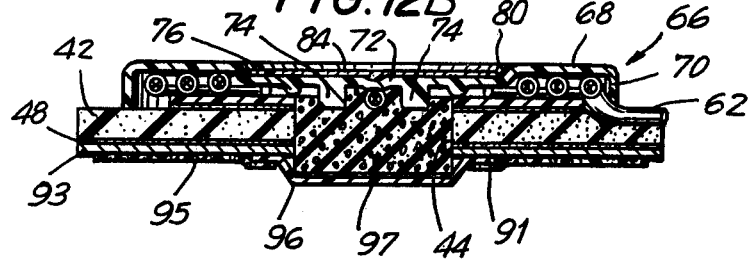

DEVICE FOR TRANSMITTING ELECTRICAL ENERGY

BACKGROUND OF THE INVENTION

The present invention relates to devices for transmitting electrical energy as well as to methods for manufacturing such device.

In particular, the present invention relates to devices which are intended to transmit electrical energy between a suitable electrical instrument and a living body such as a human body.

As is well known, there are many occasions where it is required to transmit electrical energy between an electrical instrument and an area such as an outer surface area at the skin of a human being or the like. For such purposes it is conventional to use elongated conductors having at their ends metallic components for making contact on the one hand with the skin surface and on the other hand with a suitable electrical instrument. However, conventional devices of this type suffer from a number of drawbacks. Thus, when placing a metallic element in engagement with human skin, with a suitable liquid or paste situated between the metallic element and the skin, an electrical contact of undesirably high resistance is produced and at the same time there is considerable discomfort to the individual to whom the metallic member is applied. In addition, certain inconveniences are involved in connecting an elongated flexible conductor to the metallic member which is placed in engagement with the skin, through a suitable conductive layer of paste or liquid. Furthermore, if it is desired to make X-rays such as X-rays of the chest, while the metallic contact member engages the skin, this contact member will show up in the X-ray since it is opaque to the X-rays, and thus considerable inconvenience is involved under these particular conditions where it is desired to make an X-ray of an individual to whom an electrical conductor is connected in the manner described above. Metallic contact elements of this type when placed in engagement with the skin, as through a suitable paste or liquid layer which is electrically conductive, result in an electrode which is polarizable and has an undesirable junction potential or voltage, which may be an undesirable source of inaccuracy in the electrical values which are displayed at the electrical instrument.

SUMMARY OF THE INVENTION

It is accordingly a primary object of the present invention to provide a structure which will avoid the above drawbacks.

In particular, it is an object of the present invention to provide a structure according to which a conductor is capable of transmitting electrical energy while avoiding the drawbacks set forth above in connection with conventional conductor assemblies.

Thus, it is a particular object of the present invention to provide a conductor capable of being electrically connected in a circuit with human skin or the like without requiring the use of metallic contact members or electrodes for this purpose.

A further object of the present invention is to provide a conductor of this type which has at the vicinity of the human skin or the like with which electrical contact is to be made an exposed conductor portion which can either directly engage the human skin or which can be placed in electrical contact therewith through a suitable electrically conductive gel.

Furthermore it is an object of the invention to provide a construction according to which both the electrode which cooperates with human skin or the like and the conductor extending therefrom are made of a single unitary structure.

In addition, it is an object of the present invention to provide a construction according to which it becomes possible to take X-rays, for example, while the structure of the invention is connected to the skin, without changing in any way the X-ray photograph. In other words, it is an object of the invention to provide a construction which is radio-luscent, so that it will not be seen in conventional X-rays.

Furthermore, it is an object of the present invention to provide a construction of the above type which is extremely inexpensive as well as highly reliable in use.

While it is possible for the invention to take various forms, the primary structure of the invention includes an elongated conductor made of substantially pure carbon and having at one end a region which forms the electrode to be placed in an electrical circuit with human skin or the like.

BRIEF DESCRIPTION OF DRAWINGS

The invention is illustrated by way of example in the accompanying drawings which form part of this application and in which:

FIG. 8 is a partly fragmentary illustration of how parts of the structure shown in FIG. 7 are assembled;

FIG. 9 is an illustration of a spool-forming component of FIG. 7;

FIG. 10 is a top plan view of the assembled structure of FIG. 7;

FIG. 11 is a transverse sectional illustration of part of the structure of FIG. 10 taken along line 11—11 of FIG. 10 in the direction of the arrows; and FIGS. 12A and 12B respectively are sectional elevations of further embodiments of the invention.

DESCRIPTION OF PREFERRED EMBODIMENTS

Figure 1:
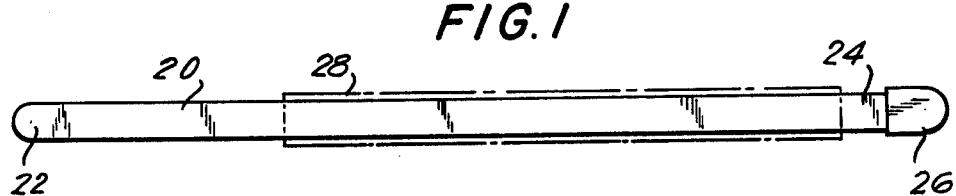
FIG. 1 is an illustration of one possible embodiment of a structure for transmitting electrical energy.

Referring to FIG. 1, there is shown therein an extremely simple embodiment according to which an elongated flexible electrical conductor takes the form of a thin, flexible strip 20 made of pure carbon which preferably is in the form of graphite. This elongated strip 20 may very simply be cut from a thin graphite sheet. One elongated end portion 22 of the electrically-conductive elongated flexible means formed by the strip 20 is exposed so as to be available for contact with the human skin, for example. Thus the portion 22 is large enough to provide adequate electrical contact directly with the skin, if desired. The opposed free end portion 24 of the strip 20 is adapted to make electrical contact with a suitable instrument such as an electrical recording instrument or the like. For this purpose the end portion 24 may carry a metallic contact clip 26 or the like which can be fastened in any suitable way to the end portion 24 so as to facilitate electrical contact with the electrical instrument.

Between the free exposed end portions 22 and 24, the elongated strip 20 is covered by an insulating means 28 which is shown in phantom lines. This insulating means can take the form of a lacquer coating or a suitable tubular plastic sheath through which the strip 20 passes so that its free end portions 22 and 24 are exposed beyond the ends of the tubular sheath or beyond the ends of the lacquer coating.

It is to be noted that a number of advantages are achieved by way of the structure shown in FIG. 1 for transmitting electrical energy. Thus, the use of pure carbon, preferably in the form of graphite, affords an extremely low electrical resistance which is orders of magnitude lower than can ever be achieved by such expedients as, for example, adding carbon to plastic or other non-conductive material. Moreover, the use of graphite in particular is highly advantageous because of its structural properties and physico-chemical inertness. The use of a single continuous carbon structure both for contact with the human skin, so as to form an electrode at the free end portion 22, and as an electrical lead or cable to the recording equipment or the like provides an electrode-lead apparatus which is radio-luscent, or in other words which cannot be seen on conventional X-rays. Thus it is possible to take a chest X-ray, for example, while the structure shown in FIG. 1 is in engagement at its end 22 with human skin at the region of the chest. The use of carbon, rather than metals, to provide an electrode results in a structure which is non-polarizable and therefore has no junction potential or voltage, so that a superior stability is achieved at the electrical display.

This free end portion 22 which forms the electrode can be placed directly in contact with the skin, requiring only a suitable strip of adhesive placed over the portion 22 and in contact with the skin to maintain the portion 22 at the proper location, eliminates the requirement of an intervening electrolyte, gel, or other liquid-phase conductor. Such a use of the structure of the invention is particularly feasible as a result of the natural tendency of carbon, particularly in the form of graphite, to shed itself, blackening the skin and creating an excellent electrical contact.

Thus, the use of carbon in connection with the electrical probes, contacts, or electrodes is of considerable advantage inasmuch as it is possible in this way to avoid the primary disadvantages encountered with metal-containing electrodes. The latter disadvantages which are overcome by carbon are disadvantages such as the existence of polarization potential at the metal interface with the active medium and the opacity of metal with respect to X-rays, as well as the disadvantage of the presence of a variable, often high, contact resistance between metal with tissue, particularly human skin. Carbon does not suffer from any of these deficiencies. Even though carbon is an excellent electrical conductor at the same time carbon is amphoteric, being an electron donor in certain circumstances and an electron acceptor in other conditions. The interface between carbon and biologic tissue has a negligible polarization potential since there is no ionic form of carbon to create a carbon-to-carbon interface. Of course, there is the additional advantage that carbon is virtually radio-luscent with respect to X-radiation.

The allotropic form of carbon best suited to the fabrication of certain types of electrodes, probes or contacts is graphite. The hardness and structural integrity of graphite permitted to be formed, shaped, and machined. Graphite can be fabricated in rods, blocks, sheets, or the like, and its structural integrity permits it to be punched, threaded, or held by crimped parts.

Moreover, there is with graphite the additional advantage of natural lubricity, resulting from the tendency of the graphite to shed at its outer layer of carbon atoms. It is this latter property which results in a black deposit when the skin is rubbed over carbon, including the graphite formed thereof. While metallic electrodes frequently require that a conductive liquid or gel be applied to the skin to permeate its cornified and lipid layers, carbon naturally sheds material from its surface which enters the superficial layers of the skin, thereby improving the conductivity between the carbon electrode and the dermis.

Figure 2:
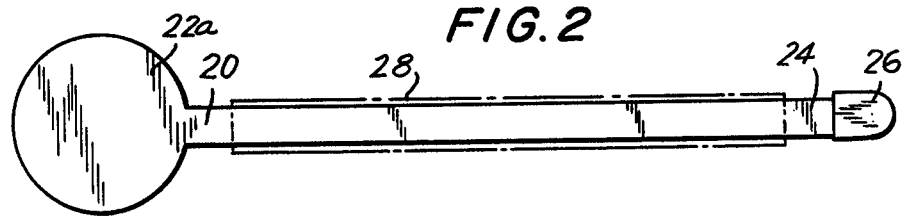
FIG. 2 illustrates another embodiment of this structure.

Referring now to FIG. 2, the structure illustrated therein is substantially the same as that of FIG. 1, with the exception of the end portion 22a of FIG. 2, which corresponds to the end portion 22 of FIG. 1. Otherwise the remaining structure is the same and is designated by the same reference characters. It will be seen that the end portion 22a is of a circular configuration having a diameter much greater than the width of the remaining part of the strip 20, so that through this expedient it is possible to achieve a desirable large area of contact between the skin and the electrode formed by the end portion 22a.

Figure 3A:
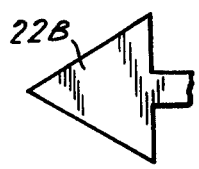
FIGS. 3A and 3B respectively illustrate different configurations for part of a structure of FIG. 2.
Figure 3B:
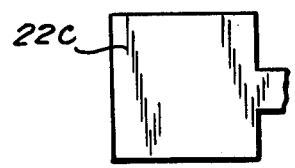

FIGS. 3A and 3B are also substantially identical with the structure of FIG. 1 except for the configuration at the free end portion which forms the electrode to contact the skin. Thus it will be seen that in FIG. 3A the end portion 22b is of a triangular configuration whereas in FIG. 3B the end portion 22c is of a substantially rectangular or square configuration, and thus through any of these expedients it is possible to enlarge the area of the end portion of the graphite strip so as to increase the area of contact with the human skin.

Figure 4:
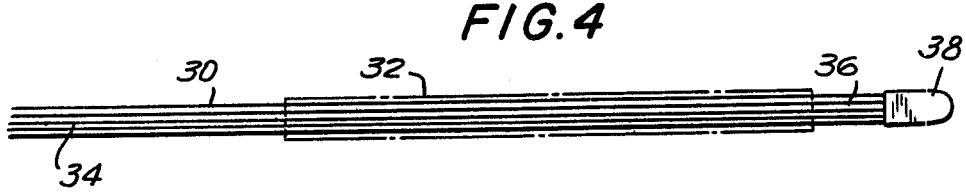
FIG. 4 is an illustration of a further embodiment of a structure for transmitting electrical energy.

It is not essential to utilize a conductor in the form of a narrow strip cut from a graphite sheet or the like. Thus, FIG. 4 illustrates an embodiment according to which a plurality of pure carbon yarns 30 are arranged in a bundle. The pure carbon yarns 30 also may be in the form of graphite, and the yarns may be twisted or untwisted as desired. These yarns 30 extend through an insulation means 32 which may be identical with the insulation means 28. Thus, the insulation means 32 leaves exposed at the yarns 30 an elongated free end portion 34 adapted to be placed in contact with the skin and an elongated free end portion 36 carrying a metallic tab 38 in order to make a suitable electrical contact with a recording instrument or the like. Thus, in FIG. 4 the elongated flexible conductor is formed of a group of fibers, thread, or yarn, which is another form in which pure carbon is available as a structural element.

Figure 5:
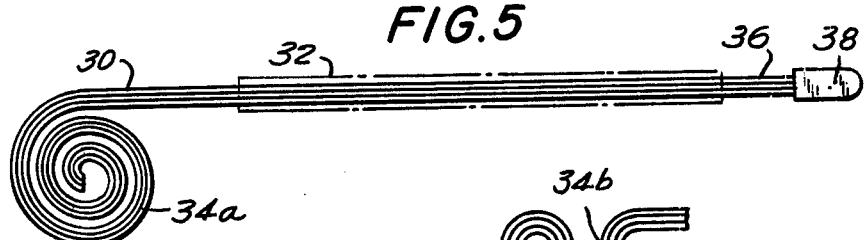
FIG. 5 is an illustration of a still further embodiment.
Figure 6:
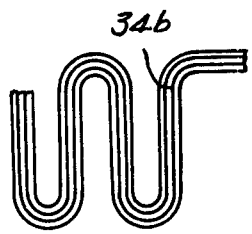
FIG. 6 is a fragmentary illustration of another possible configuration for part of the structure of FIG. 5.

In FIG. 4 the carbon structure is shown in a straight linear form, similar to FIG. 1. However it is also possible to provide arrangements as shown in FIGS. 5 and 6. Thus, in FIG. 5 the fibers or yarns 30 are the same as those of FIG. 4. The only difference between FIG. 5 and FIG. 4 resides in the fact that instead of a free end portion 34 which is straight as shown in FIG. 4, the end portion 34a of FIG. 5 is in the form of a spiral. The yarns are wound into a tight spiral 34a to create in this way an enlarged circular area of contact with the skin. It is also possible to provide parallel courses of the yarn forming an end portion 34b, as shown in FIG. 6, in order to increase the area of contact with the skin, these parallel courses extending in opposite directions back and forth to create a substantially rectangular area for the end portion 34b of the embodiment of FIG. 6. Of course other configurations are possible in order to increase the area of contact with the skin.

As will be apparent from the description below it is also possible to utilize a conductive gel, and the use of such an expedient in connection with the yarn form of the carbon is particularly desirable because the gel will have the capability of completely surrounding the yarn while having a large area of contact with the skin. As was indicated above an adhesive pad or tape may be utilized to maintain the carbon in intimate contact with the skin.

Thus, according to the basic concept the invention provides a single unitary carbon element which serves as a body electrode, as an electrical lead extending from the body electrode, and as an electrical connector, with the total length of the conductor being sufficient to span the full dimension of the torso so that complete lucency to X-ray of the subject can be provided. Together with a thin insulation of a proper plastic it is possible to provide a unitary electrode of pure carbon which is non-polarizable and which is at the same time radio-luscent.

A further embodiment of the invention is illustrated in FIGS. 7-11. This embodiment includes a support means 40 which is indicated in FIG. 11. The support means 40 includes a foam pad 42 made of any suitable foam plastic and having the circular configuration illustrated most clearly in FIG. 7. The foam pad 42 is formed with a central opening 44 in which a conductive gel is situated. FIG. 11 shows the conductive gel 46 situated in the central opening of the foam pad 42 of the support means 40. This support means has an outer face adapted to engage the skin. For this purpose the foam pad 42 carries an adhesive layer 48 at its surface which is not visible in FIG. 7, and by way of this adhesive layer is is possible for the foam pad to reliably adhere to the skin.

The support means includes in addition to the foam pad 42 a plastic member 50 in the form of a disc of thin flexible plastic sheet material. The foam plastic pad 42 and the disc 50 may both be made of polyethylene, for example. The disc 50 is formed with a central opening 52 of the same diameter as the opening 44. At its surface which is not visible in FIG. 7, the disc 50 has a layer of adhesive, and the disc 50 is assembled with the pad 42 simply by being adhered to the top surface of the pad 42 which is visible in FIG. 7. These components when they are thus joined together have their openings 44 and 52 coaxially aligned so that together they form for the support means 40 an opening extending inwardly into the support means from the outer face thereof which is formed by the adhesive layer 48. It is this opening which is occupied by the gel 46 illustrated in FIG. 11.

When the components 42 and 50 of the support means 40 are assembled together, the elongated, flexible electrically conductive means 54 is then added to the assembly. This elongated flexible electrically conductive means corresponds to the structures shown in FIGS. 1-6. Thus, the means 54 includes an elongated flexible carbon yarn 56. Situated next to the yarn 56 and extending along the latter coextensively therewith is a reinforcing yarn 58 made of a suitable plastic such as a suitable polyamide. For example the reinforcing yarn 58 may be made of nylon or it may be made of a polyamide material known as Kevlar. These yarns are situated in a flexible plastic tube in the form of a sheath which insulates the electrically conductive carbon yarn 56. Of course the yarn 56 and 58 may be simply straight or they may be twisted as desired. The insulating sheath 60 may also be made of polyethylene. Thus, in order to obtain the electrically conductive means 54 with the insulation means 60 assembled therewith, it is only necessary to direct the yarns 56 and 58 through a suitable extruding die while the sheath 60 is directly extruded onto the yarns as they progress through and beyond the die, and in this way it is possible to achieve in an inexpensive manner the means 54. This assembly of the yarns 56 and 58 together with the insulating sheath 60 is cut into suitable lengths. The right free end of this length then has a portion of the sheath 60 removed so as to expose the yarns 56 and 58. A suitable metallic connector tab 62 is then fixed to the exposed yarns to form an electrical connection similar to the tabs 26 shown in FIGS. 1 and 2. A simple hollow pin of metal may form the element 62, this pin receiving in its interior the yarns 56 and 58. With these yarns thus situated within the metal tube, the latter is suitably crimped so as to be fastened with the yarns, thus forming in this simple way a suitable connector tab to be connected with an electrical instrument such as a recorder.

Figure 7:
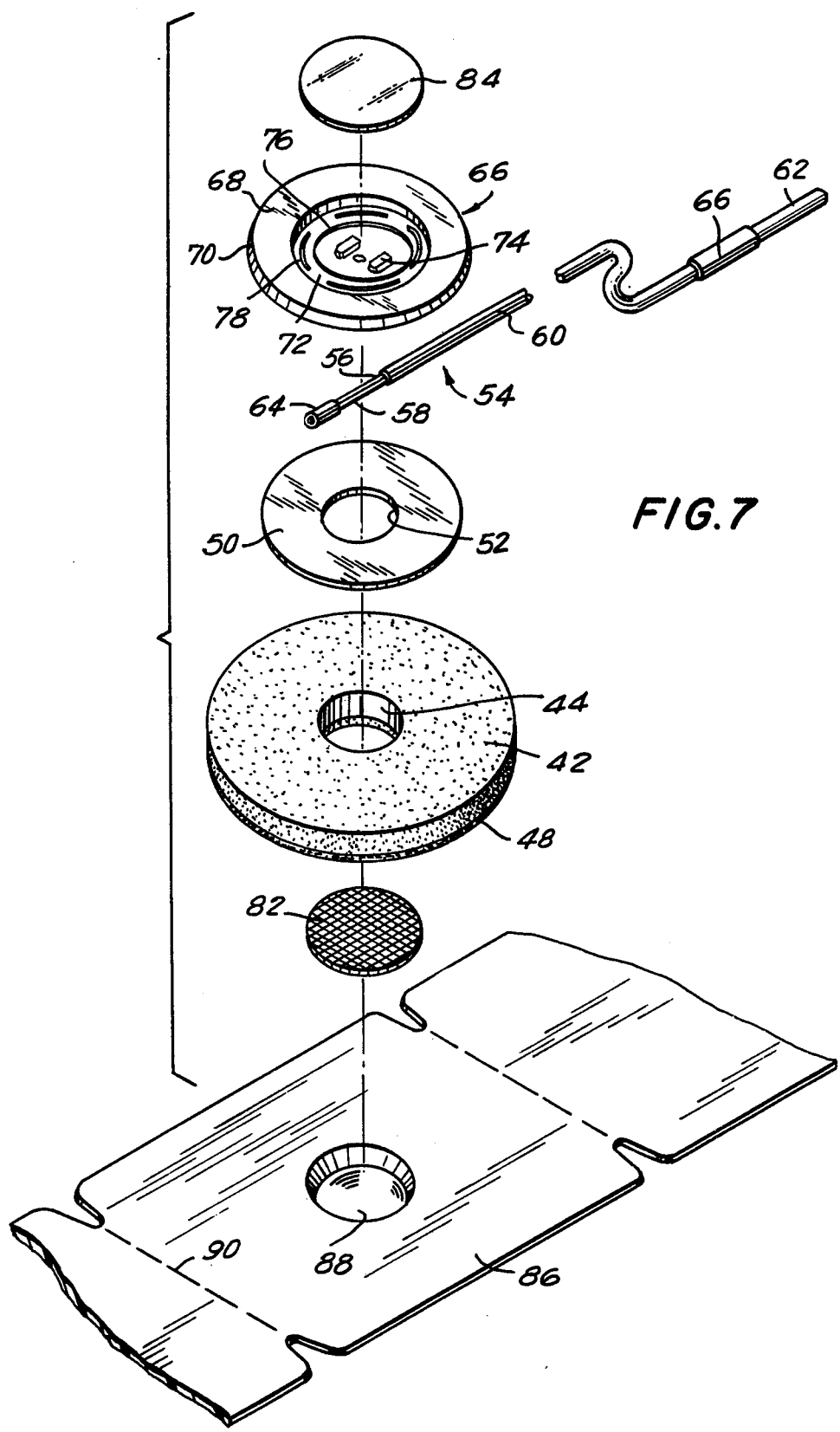
FIG. 7 is an exploded perspective partly fragmentary illustration of a still further embodiment of the invention.

At the opposite end of the yarns 56 and 58, a relatively short portion of the insulation sheath 60 also is cut away and removed. This is done simply by forming a circular cut through the wall of the sheath 60 and removing a portion thereof from the yarns so as to expose a free end portion thereof. Then a second circular cut is made through the wall of the sheath 60, so as to provide in this way a length 64 of the sheath 60, and this length is then simply shifted so as to cover the free ends of the yarns 56 and 58 from which the original portion of the insulating sheath was removed. In this way there is provided a structure as shown in FIG. 7 according to which between the longer sheath 60 and the separate portion 64 thereof there is an exposed portion of the electrically conductive carbon yarns 56 as well as an exposed portion of the reinforcing yarn 58. If desired a suitable color-coded band 66 may be placed around the insulating sheath 60 adjacent the conductive tab 62 for strength and strain relief as well as for coding purposes as may be required.

With the means 54 thus manufactured in the above manner, it is in a condition to be joined with the support means 40. For this purpose the sheath 60 and the separated portion 64 thereof are arranged directly in contact with the exposed surface of the disc 50 in the manner shown in FIG. 8. Of course the disc 50 will have been already adhered to the pad 42. Thus it will be seen that the exposed portions of the yarns 56 and 58 extend across the opening 52 as well as the opening 44 in the pad 42. With the insulating portions 64 and 60 thus placed in engagement with the surface of the disc 50 as shown in FIG. 8, these portions 60 and 64 are adhered or welded to the disc 50 as by using cement, heat, etc., so that by way of this welding a secure connection is made between the insulation and the disc 50. In this way through the insulation the support means 40 supports and carries the conductor 56.

When the assembly has been completed up to the stage shown in FIG. 8, a spool-forming means 66 is then assembled with the structure. This spool-forming means 66 takes the form of a circular plastic member having a circular wall portion 68 which is spaced from the disc 50 so as to define therewith a space within which coils of the insulated cable or yarn 54 can be situated in the manner shown most clearly in FIGS. 10 and 11. This circular wall portion 68 of the plastic member 66 terminates at its outer peripheral circular edge in a lip 70 which extends down freely into engagement with the foam pad 42, and it will be noted that the diameter of the member 66 is such that the lip 70 is situated outwardly beyond the outer peripheral edge of the disc 50 while still being situated inwardly of the outer peripheral edge of the pad 42.

The circular wall portion 68 surrounds a depressed portion 72 of the plastic wall member 66, this depressed portion 72 being of a circular configuration and extending over the part of the cable previously joined to the disc 50 in the manner described above. At its face which is directed toward the disc 50 the plastic flexible wall member 66, which may also be made of polyethylene, has a pair of bosses 74 which are integral with the remainder of the member 66 and which define between themselves a space in which the exposed portion of the conductor 56 can conveniently be located. Outwardly beyond the bosses 74 the wall member 66 has a circular rib 76, and outwardly beyond the latter a plurality of arcuate ribs 78, these ribs also being formed integrally with the remainder of the plastic wall member 66. It is these ribs 76 and 78 which directly engage the plastic disc 50 to become welded thereto. Thus after first welding the sheath to the disc 50, the plastic wall member 66 is welded to the disc 50 along the ribs 76 and 78, and in this way the spool-forming means 66 becomes reliably fixed with the disc 50, connected through the latter to the pad 42, so as to form in this way a spool in which coils of the insulation means 54 can be situated. It will be noted that the wall portion 68 and the depressed portion 72 are joined by a substantially frustoconical portion 80 of the plastic wall member 66, and it is this portion 80 which forms the inner circular wall of the spool around which the innermost coil of the cable 54 is situated. Thus, with the spool-forming means 66 assembled with the support means 40, it is possible to wind the cable so that it assumes the configuration apparent from FIGS. 10 and 11 according to which the cable is wound in the form of a spiral, and the free end portion of the cable where the contact 62 is located can simply extend freely through the space between the pad 42 and the lip 70, the components 66 and 42 being capable of flexing freely for the purpose of passage of the cable 54 into or out of the space between the wall member 60 and the disc 50 and pad 42.

With the structure thus assembled, a gel which is well known and which is electrically conductive is introduced into the opening 46 as well as into the opening 52 and further toward the spool-forming means 66 into engagement with the bosses 74 and intimately surrounding the electrically conductive carbon yarn 56 so that a highly reliable electrical connection is made therewith through the electrically conductive gel 46 which is shown in FIG. 11.

In order to retain the semi-solid gel in the opening of the support means in intimate contact with the carbon yarn 56, a porous cover member 82 is provided. This member 82 has a diameter somewhat larger than the diameter of the opening 44 and it is in the form of a suitable mesh of fabric or plastic yarns, the openings of the mesh being sufficient to provide for a large area of contact between the gel 46 and the skin while at the same time the mesh 82 will serve reliably to retain the gel assembled with the support means. The outer peripheral edge of the porous cover member 82 which extends beyond the opening 44 will be reliably adhered to the pad 42 by way of the adhesive layer 48 referred to above.

The depression portion 72 of the spool-forming means 66 affords a suitable recess in which it is flexible to situate an identifying disc 84 made of a suitable cardboard or paper and carrying a color or other identification which may be coordinated with the color-coated band 66.

For packaging, storing, and shipping purposes the srcuture described above and shown in FIG. 7 is assembled with a plastic sheet material 86 formed with a suitable blister recess 88. This sheet material 86 may also be made of polyethylene and when it is thermo-formed the blister recess 88 can be provided. This blister 88 becomes aligned with the porous cover member 82 and serves to protect the latter as well as the gel 46 during shipment and storing of the device. The adhesive layer 48 adheres to the surface of the sheet 86 which surrounds the blister recess 88 thereof, and in this way the structure can be stored over an extremely long period of time. When it is desired to use the structure, the sheet 86 is simply peeled away from the pad 42 in order to leave exposed the adhesive layer 48 which can then be applied to the skin. It is preferred to provide an elongated strip 86 of the plastic sheet material having three portions separated by the perforated lines 90, as indicated in FIG. 7, and each of these three portions are identical with the central portion shown in FIG. 7 and having the blister 88. Thus the structure can be provided in groups of three and shipped in this way with each unit being separable from the other by tearing along the line of perforations 90, and then when it is desired to use the structure the sheet 86 is peeled away from the adhesive layer 48 thus providing a unit as described above and capable of being used in the manner described above.

When this structure of the invention is applied to the skin, the gel will have intimate contact with the skin through the small pores or apertures of the mesh 82, and since the gel has an intimate contact with the carbon yarn 56, a highly reliable electrical connection is made achieving all of the results of the invention set forth above. It will be noted that all of the components of the structure are non-metallic so that radio-luscency is maintained.

Of course, more than one electrically conductive carbon yarn can be provided and more than one reinforcing plastic yarn can also be provided, and these yarns can be twisted or not as desired.

FIGS. 12A and 12B respectively illustrate embodiments where instead of the cover 82, an open-cell foam plug 97 is introduced into the opening 44 while of course being surrounded by the adhesive layer 48. This open-cell foam plug 97 is filled throughout its interstices with gel which is electrically conductive, and this plug extends also through or at least into the opening 52 so that the carbon conductor 56 directly engages the electrically conductive gel. As is apparent from FIGS. 12A and 12B the plug 97 extends somewhat beyond the adhesive layer 48 so as to make a good contact with the skin when the pad 42 is applied to the skin.

Instead of having a plurality of blister-type carriers for a series of the articles as described above, it is possible also to have single gel-foam protecting blisters, as indicated in FIGS. 12A and 12B. Thus, such a construction will be provided in order to protect one electrode at a time, in the event that a single-unit mode of packaging is desired. The blister 89 shown in FIG. 12A is adhered directly to the adhesive layer 48 and is shown as accommodating the plug 97 where it projects beyond the layer 48, as is apparent from FIG. 12A. Otherwise, the construction of FIG. 12A is identical with that described above.

With respect to FIG. 12B, instead of a single blister layer 89, there is a blister-type of protecting layer 96 the outer diameter of which is much smaller than the element 89, this blister-type of protective layer 96 accommodating the plug 97 in the same way as the layer 89 but being adhered to the layer 48 only at the inner peripheral region thereof. Thus, this element 96 has an outer lip portion 91 the diameter of which is only slightly greater than the diameter of the opening 44. According to this embodiment the blister 96 is adhered to a suitably treated release paper 93, the treated side of which directly contacts the adhesive layer 48. A circular ring-shaped adhesive paper element 95 is directly adhered to the exterior surface of the lip 91 as well as to the outer surface of the release paper 93 at the untreated surface of the latter. Thus, with this construction the release paper 93 can be peeled away from the adhesive layer 48 while simultaneously removing the blister component 96, thus exposing the adhesive layer 48 and the gel-filled foam plug 97 so that these components can be applied directly to the skin.

In both of the embodiments of FIGS. 12A and 12B, the open cell foam plug 97 can be directly welded to the bosses 74.

The above-described structure of the invention can be manufactured at relatively low cost to provide an extremely effective structure for transmitting electrical energy between a surface such as the surface of human skin and an electrical instrument.

What is claimed is:

1. In a device for transmitting electrical energy, support means having an outer face adapted to be placed in engagement with a surface such as a human skin surface, said support means having an outer peripheral edge surrounding said outer face thereof and being formed inwardly of said outer peripheral edge with an opening extending at least partly into said support means from said outer face thereof, an electrically-conductive gel situated in said opening of said support means and being at least partly exposed at said outer face of said support means for engaging and making electrical contact with the surface engaged by said outer face of said support means, at least one carbon yarn having an unattached, non-insulated, exposed portion situated at said opening in said gel and engaged thereby for making electrical contact therewith, electrical insulation means covering said carbon yarn at the region of the non-insulated portion thereof situated in said gel, said insulation means being fixed to and carried by said support means for supporting said carbon yarn through said insulation means while protecting said carbon yarn from mechanical stresses, said yarn together with said insulation means having a length sufficiently great to extend through a substantial distance beyond said support means, and said carbon yarn carrying at an end portion distant from said portion in said gel a contact means for making electrical contact with an electrical instrument or the like, said contact means being situated next to an end of said insulation means which is distant from said non-insulated portion of said carbon yarn.

2. The combination of claim 1 and wherein said support means has a layer of adhesive at said outer face thereof.

3. The combination of claim 1 and wherein at least one plastic yarn extends alongside said carbon yarn coextensively therewith, for reinforcing said carbon yarn, said insulation means covering both of said yarns.

4. The combination of claim 1 and wherein said insulation means includes an electrically non-conductive sheath having spaced portions between which the non-insulated portion of the carbon yarn in said gel extends, said support means including a member formed with an opening aligned and communicating with said opening which extends from said outer face of said support means, and said sheath being joined at said spaced portions thereof to said member.

5. The combination of claim 4 and wherein said support means includes a foam pad having opposed to said outer face of said support means a surface to which said member is fixed, said member being in the form of a disc of sheet material.

6. The combination of claim 5 and wherein said foam pad has a surface opposed to said disc and carrying a layer of adhesive which forms said outer face of said support means.

7. The combination of claim 6 and wherein a porous cover member is situated at said outer face of said support means, extending across said opening which extends inwardly from said outer face of said support means, said porous cover member having an outer peripheral edge region fastened by said adhesive layer to said foam pad and the gel within said opening of said support means extending through smaller openings of said porous cover member for directly engaging a human skin surface or the like while said porous cover member retains said gel in said opening of said support means.

8. The combination of claim 7 and wherein said porous cover member is in the form of a circular sheet of mesh material.

9. The combination of claim 6 and wherein an open-cell foam plug is situated in said opening which extends inwardly from said outer face of said support means and is filled with said gel for directly engaging a human skin surface or the like while retaining said gel in said opening of said support means.

10. The combination of claim 5 and wherein said foam pad is of a circular configuration an has its outer peripheral edge surrounding said disc, the latter being of a smaller diameter than said foam pad and being coaxially situated with respect thereto, said disc being adhered to said surface of said foam pad which is opposed to said outer face thereof, and spool-forming means connected with said disc and cooperating with the latter and said foam pad to form therewith a spool in which said carbon yarn and insulation means covering the same are wound when stored prior to use.

11. The combination of claim 10 and wherein said spool-forming means includes a plastic wall member having a circular wall portion substantially parallel to said disc and situated opposite but spaced from said disc to define with the latter a space in which coils of said yarn and insulation means may be situated, said wall member having an outer peripheral lip extending from said circular wall portion thereof into close proximity with said foam pad beyond said disc so that the yarn together with the insulation means covering the same can pass freely between said lip and said foam pad when unwound from the space between said circular wall portion of said plastic wall member and said disc, said plastic wall member having an inner depressed portion surrounded by said circular wall portion and situated closer to said disc than said circular wall portion of said plastic wall member, said inner depressed portion extending across said opening of said disc and said opening of said foam pad in which the gel is situated and said depressed inner portion being welded to said disc.

12. The combination of claim 11 and wherein said plastic wall member has at said depressed portion thereof ribs extending into engagement with said disc and welded to the latter.

13. The combination of claim 12 and wherein said plastic wall member has at the surface of said depressed portion which is directed toward the gel a pair of bosses between which the exposed portion of the carbon yarn which is in said gel is situated.

14. The comination of claim 13 and wherein said foam pad has an outer peripheral edge situated outwardly beyond said lip.

15. The combination of claim 14 and wherein a sheet of plastic material is adhered to said adhesive layer at said outer face of said support means for storing the latter for use, said sheet of plastic material being peeled away from said adhesive layer to expose the latter for contact with an area of human skin or the like.

16. The combination of claim 14 and wherein said sheet of plastic material has a blister portion aligned with said opening of said support means and said gel therein to protect the latter.

* * * * *